United States Patent [19]

Pryslak

[11] Patent Number: 4,879,547
[45] Date of Patent: Nov. 7, 1989

[54] GAS ZONE VALVE EMERGENCY ALARM SYSTEM

[75] Inventor: August J. Pryslak, Denver, Colo.

[73] Assignee: Valve Alert Systems, Inc., Englewood, Colo.

[21] Appl. No.: 251,126

[22] Filed: Sep. 29, 1988

[51] Int. Cl.$^4$ .................. G08B 21/00; F16K 37/00
[52] U.S. Cl. .................................. 340/686; 340/500;
340/619; 340/603; 116/277; 350/356; 350/484;
350/96.2; 350/96.23; 200/61.86; 261/DIG. 74;
251/369; 137/551; 137/555; 137/556
[58] Field of Search ............... 340/326, 500, 501, 603,
340/606, 610, 618, 619, 555, 557, 687, 686;
137/551, 556, 553, 556.3, 556.6; 350/355, 353,
359, 96.1, 484, 96.21, 96.2, 356, 96.22–96.29;
116/277; 251/356, 369; 261/DIG. 74, DIG. 53;
200/61.85, 61.86

[56] References Cited

U.S. PATENT DOCUMENTS 4,185,886  1/1980  Corrales ............................ 350/96.21
4,358,960  11/1982 Porter ................................... 356/375
4,573,115  2/1986  Halgrimson ..................... 340/825.06

OTHER PUBLICATIONS 55-131744, 10-1980, Japan, Seisakusho et al, 116-277.

Primary Examiner—Donnie L. Crosland
Attorney, Agent, or Firm—Sheridan, Ross & McIntosh

[57] ABSTRACT

The system includes a plurality of zone valves located in a gas flow pipeline. These valves contain a fiber optic bundle that is installed in the center of the valve handle. The fiber optic light comes from a source and is read by a light detector. As long as light is detected by the light detector, the circuitry within the detector will function as a closed circuit. As soon as the detector is not sensed, the detector will function as an open circuit and will provide an alarm to a floor control panel and on to a system annunciator. The system processor is capable of performing remote shunting. The operator can determine by visual reference the location of the problem. False alarms caused by intermittent faulty loops can be identified by a built in memory circuit. The circuit is also capable of detecting loss of current flow that could be caused by a number of reasons. The loss will cause an alarm condition to occur and the operator shall be notified of the system's condition.

13 Claims, 2 Drawing Sheets

GAS ZONE VALVE EMERGENCY ALARM SYSTEM

This invention pertains to emergency alarm systems, and in particular to such emergency alarm systems relating to gaseous line zone valve emergency alarm systems that notify users when a supply of a gas, such as oxygen has been shut down on purpose or by accident.

The field of emergency alarm systems has many applications, but an area of concern has recently arisen. The use of shut-off valves in gaseous systems is well known and, in fact, is required by many statutory bodies. For example, oxygen lines in hospitals have to have emergency shut-off valves in areas that are accessible to hospital personnel so that they may be able to shut the lines down in case of a fire or similar emergency. The problem that can occur is that, if a line is accidently shut down and the hospital personnel are not aware of that fact, an individual who requires that oxygen can be put at serious risk. There have been examples of deaths that have occurred when people being operated on have died when they have been deprived of oxygen for any period of time. Examples of these emergency alarm systems include the Patent issued to Joseph Vandeweghe, #4,074,225 issued on Feb. 14, 1978 for an Emergency Detection Alarm and Evacuation System. This system provides a plurality of spatially distributed detectors and exit indicators that can be controlled at a centrally located control center and also uses a closed circuit television system. Another example of a device which provides an emergency alarm system is the United States patent issued to Thomas S. Wootton, #3,689,888 for a Pulse Position Modulated Alarm System, issued on Sept. 5, 1972. This device teaches a radio transmission link alarm that monitors a number of remote locations. The information is received and disseminated at a central location. The drawback of these devices is that they deal with alarm systems that would not lend themselves to valves in gaseous pipeline systems as effectively as applicant's device.

Clearly, it is desirable for a gas zone valve emergency alarm system that does not contain the limitations described above and at the same time is simple and practical to operate. It is the object of this invention, then to set forth an improved emergency alarm system which avoids the disadvantages and limitations, above-recited, which exist in current emergency alarm systems.

It is also the object of this invention to teach a gas zone valve emergency alarm system that uses a constant light source to close or open the alarm systems. It is another object of this invention to teach a gas zone valve emergency alarm system that is simple to install and easy to operate and, at the same time, be able insure system integrity. Particularly, it is the object of this invention to set forth a gas zone emergency alarm system, for operative installation in a structure having gaseous pipelines installed, comprising at least one valve; said valve comprises shut-off means for cutting off gas flow in emergency situations; said valve has housing means; said valve further has a constant light source; said valve has a constant light transmitting means; said light transmitting means comprises a fiber optic bundle; said valve further has a constant light detection means; said light detection means has means for indicating the completion of a closed circuit; said light detection means further has reporting means for alerting the operators of an open circuit; data transmission means; means for receiving data from said data transmission means; said data receiving means comprises an annunciator panel; said annunciator panel has site location means; said annunciator panel further has alarm means; said alarm means comprises audio and visual notification means; said annunciator panel further has relay means for submitting notification to a centralized location; a control center; and said control center has a circuit integrity memory.

Further objects and features of this invention will become more apparent by reference to the following description taken in conjunction with the accompanying figures, in which.

Figure 1:
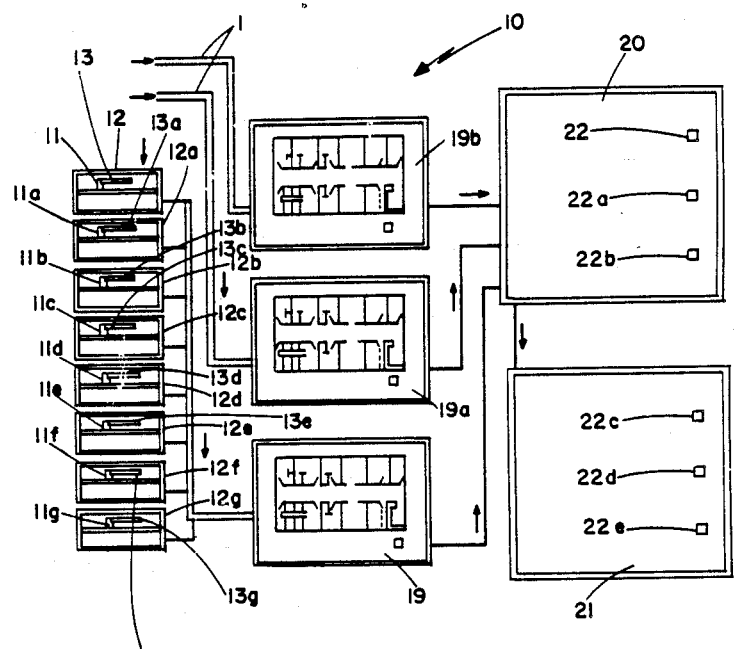
FIG. 1 is a block diagram of the novel gas zone valve emergency alarm system.
Figure 2:
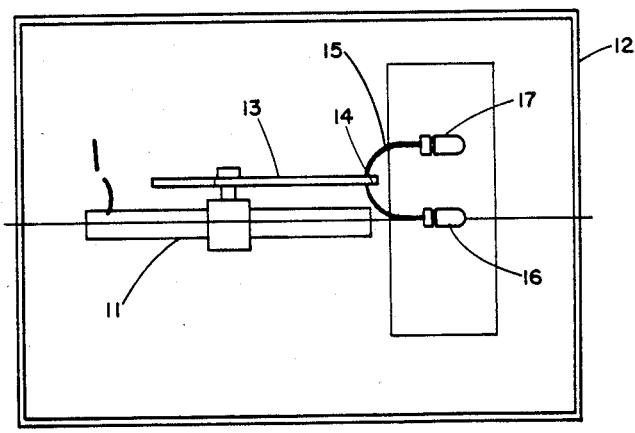
FIG. 2 is a side elevational view of a zone valve which shows the light apparatus.
Figure 3:
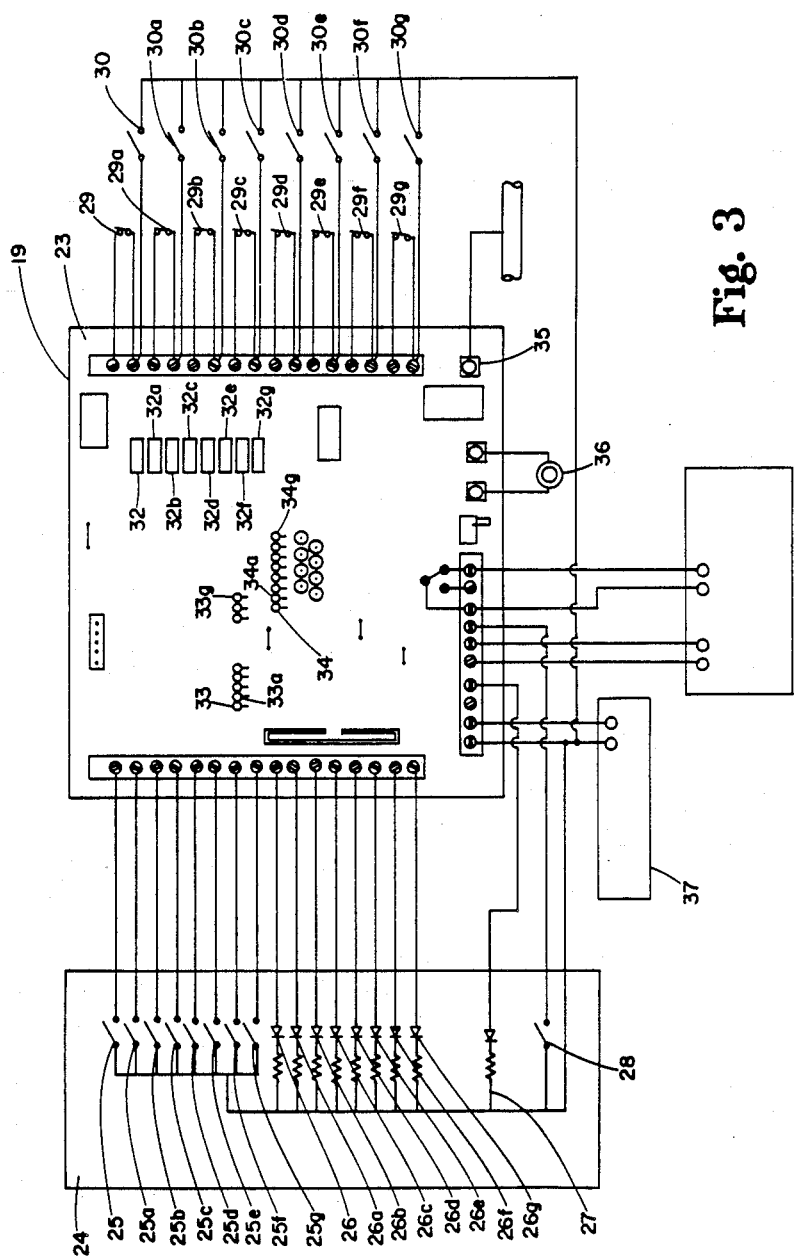
FIG. 3 is a schematic view of the circuits of the alarm system.

As shown in the figures, the gas zone valve emergency alarm system 10 comprises a plurality of gas zone valves 11 through 11g on pipelines 1 located in valve boxes 12 through 12g at accessible locations throughout a facility, such as a hospital. They are designed to enable personnel to shut off the flow of a gas, such as oxygen, in the event of an emergency or required maintenance of the pipeline system. The handles 13 through 13g of the gas zone valves have apertures (only 14 shown) through which a fiber optic bundle 15 shown is passed. That bundle carries light from a light source 16 which puts out a constant light beam through the fiber optic bundle to a light detector 17. Both the light source and the light detector are positioned on a mounting plate 18. If the handle 13 is turned to the off position (perpendicular to pipeline itself) the fiber optic bundle 15 is pulled out of the light detector 17 and the system is made aware of an open circuit.

The open circuit signal is sent through wiring to the individual floor warning panel 19 through 19b, usually located at the nurses' station on the floor, and then sent to the main control center panel 20 and a system remote panel 21 that is usually located in the building engineer's office. The floor panels 19 through 19g indicate the exact location on their particular floor of the open circuit. While the indication of the main control panel 20 and the remote panel 21 indicate only the floor on which the open circuit has occurred by means of indicator lights 22 through 22e.

The system processor 23 located on the floor panels 19, 19a, and 19b is a multi-zone annunciator that is capable of being expanded and can perform remote shunting. The remote annunciator 24 comprises a plurality of push button shunt switches 25 through 25g. Activating an individual shunt will illuminate an individual light emitting diode 26 through 26g located on the floor panel. The remote annunciator 24 has a memory circuit 27 and a reset switch 28. The system processor also has separate closed circuit loops 29 through 29g and open loop circuits 30 through 30g that are connected to each of the valve constant light systems. A slide switch 31 places the processor in a freeze reset mode or an automatic reset mode. In the freeze reset mode, the processor is in a memory mode and the LED will illuminate. In the automatic reset mode, the system will show the accurate status of the individual zones through the individual zone LED. A series of capacitors 32 through 32g are designed to provide individual loop pulse stretchers to protect the individual loops from immediate alarm in the case of momentary circuit openings. Diodes 33 through 33g allow the system to indicate an alarm condition when an individual system is being shunted. Diodes 34 through 34g provide the user with the ability to program a momentary output relay change of state for each zone violation by means of cutting a lead of the diode for that individual zone. The processor is grounded from the board at connection 35 to a ground. A system audio alarm 36 is provided and power is provided through a filtered direct current circuit 37.

The system operates in the following manner. As long as the fiber optic bundle is present in the light detector and is transmitting a constant beam of light, the solid state devices in the light detector will function as a closed circuit. When the light is broken or removed, an open circuit will occur causing an alarm to notify hospital personnel. The exact location of the valve shut off will be pinpointed on the floor panel. The panels can be connected together which allows mutable alarms assuring proper notification when an alarm occurs. The electronic circuits will detect a loss of current flow and will then illuminate warning lights and sound alarms. If the alarm is reset, and the original condition still exists, the audio alarm will be silenced but the light signal will continue to be illuminated.

While I have described my invention in connection with specific embodiments thereof, it is clearly to be understood that this is done only by way of example and not as a limitation to the scope of my invention as set forth in the objects thereof and in the appended claims.

I claim:

1. A gas zone valve emergency alarm system, for operative installation in a structure having gaseous pipelines installed, comprising:
   at least one valve for cutting off gas flow in emergency situations;
   housing means for housing said valve;
   a constant light source disposed adjacent to said valve;
   constant light transmitting means comprising a fiber optic bundle communicating with said light source;
   a constant light detection means for indicating the completion of a closed circuit and for alerting the operators of an open circuit, said light detection means being responsive to light transmitted by said light transmitting means;
   data transmission means responsive to said light detection means for transmitting data relating to whether one of a closed circuit and an open circuit exists;
   means for receiving data from said data transmission means comprising an annunciator panel, wherein said annunciator panel has site location means and alarm means, said alarm means comprising audio and visual notification means and wherein said annunciator panel further has relay means for submitting information relating to the existence of one of said closed circuit and said open circuit; and
   a control center for receiving said information from said relay means, wherein said control center has circuit integrity memory means.

2. A gas zone valve emergency alarm system, according to claim 1, wherein:
   said valve comprises a manually rotated handle means; and
   said handle means has an aperture therein.

3. A gas zone valve emergency alarm system, according to claim 1, wherein:
   said constant light source comprises a light emitting diode.

4. A gas zone valve emergency alarm system, according to claim 1, wherein:
   said fiber optic bundle is replacably inserted in said aperture of said bundle.

5. A gas zone valve emergency alarm system, according to claim 1, wherein:
   said circuit integrity memory means comprises a delay memory circuit to reduce false alarms.

6. A gas valve system, comprising:
   valve means including movable handle means, said handle means of said valve means being adapted to cut off gas flow in a predetermined situation;
   fiber optic bundle means for transmitting light and having a portion for engaging said handle means wherein, when said handle means is moved, said fiber optic bundle portion is moved; and
   light detecting means responsive to said fiber optic bundle means for indicating whether said handle means of said valve means has been moved whereby gas flow is affected by said handle means movement.

7. A system, as claimed in claim 6, wherein:
   said handle means includes an aperture through which said fiber optic bundle means portion is passed so that, when said handle means is moved, said fiber optic bundle means portion is caused to move.

8. A system, as claimed in claim 6, wherein said fiber optic bundle means includes:
   a light source; and
   fiber optics for transmitting light outputted by said light source.

9. A method for detecting the position of a gas valve connected to a pipeline for carrying gas, comprising:
   providing a valve having a handle for controlling the flow of gas;
   providing a light source;
   providing a fiber optic bundle adjacent to said handle and communicating with said light source;
   locating said handle in a first position;
   determining whether said handle should be moved to a second position when a predetermined situation is present
   causing movement of said fiber optic bundle as a result of movement of said handle when the predetermined situation is present; and
   monitoring the presence of light using light detecting means to determine whether gas flow has been affected.

10. A method, as claimed in claim 9, wherein:
    said step of causing movement includes pulling said fiber optic bundle away from one of said light source and said light detecting means.

11. A method, as claimed in claim 9, wherein:
    said step of monitoring includes identifying that an open circuit exists when said fiber optic bundle is moved.

12. A method, as claimed in claim 9, wherein:
    said step of moving includes turning said handle to a position substantially perpendicular to the pipeline for carrying gas.

13. A method, as claimed in claim 9, wherein:
    said step of providing said valve includes providing said valve having said handle with an aperture; and
    said step of providing a fiber optic bundle includes locating a portion of said fiber optic bundle through said aperture.

* * * * *